(12) United States Patent
Senapathy

(10) Patent No.: US 6,521,428 B1
(45) Date of Patent: *Feb. 18, 2003

(54) SHOT-GUN SEQUENCING AND AMPLIFICATION WITHOUT CLONING

(75) Inventor: Periannan Senapathy, Madison, WI (US)

(73) Assignee: Genome Technologies, LLC, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/434,761

(22) Filed: Nov. 4, 1999

Related U.S. Application Data

(60) Provisional application No. 60/130,358, filed on Apr. 21, 1999.

(51) Int. Cl.[7] .......................... C12P 19/34; C12Q 1/68; G01N 33/00; C07H 21/02; C07H 21/04
(52) U.S. Cl. .................. 435/91.2; 435/6; 435/91.1; 436/94; 436/23.1; 436/24.3; 436/24.33
(58) Field of Search .................... 435/6, 91.1, 91.2, 435/183; 436/94; 536/23.1, 24.3, 24.33, 25.3

(56) References Cited

U.S. PATENT DOCUMENTS

| | | | | |
|---|---|---|---|---|
| 5,552,278 A | * | 9/1996 | Brenner | ........................ 435/6 |
| 5,807,679 A | * | 9/1998 | Kamb | |
| 5,935,794 A | * | 8/1999 | Kambara et al. | .............. 435/6 |

OTHER PUBLICATIONS

Sambrook et al., Molecular Cloning: A laboratory Manual, Second Edition, Cold Spring Harbor Laboratory Press, p. 11.7, 1989.*
Dean, Frank et al., Rapid Amplification of Plasmid and Phage DNA Using Phi29 DNA . . . Methods, p. 1095–10999.*
Ball, et al., 1998 The use of tailed octamer primers for cycle–sequencing, *Nucleic Acids Research* 26:5225–5227.
Bock and Slightom, 1995.
Burbelo, P.D. and Iadarola, M.J., 1994. Rapid plasmid DNA sequencing with multiple octamer primers, *Biotechniques* 16:645–6; 648–50.
Hardin, S.H., et al., 1996. Octamer–primer cycle–sequencing: Design of an optimized primer library, *Genome Research*, 6:545–550.
Hou, W. and Smith, L.M., 1994. DNA sequencing with a hexamer string primer and dye–labeled terminators. *Anal. Biochem.* 221:136–141.
Jones, L.B. and Hardin, S.H., 1998. Octamer–primed cycle–sequencing using dye–terminator chemistry, *Nucleic Acids Research*, 26:2824–2826).

(List continued on next page.)

*Primary Examiner*—Ethan C. Whisenant
*Assistant Examiner*—Frank Lu
(74) *Attorney, Agent, or Firm*—Joseph T. Leone, Esq.; DeWitt Ross & Stevens S.C.

(57) ABSTRACT

Disclosed is a method for sequencing and amplifying nucleic acid templates wherein a degenerate primer with a fixed sequence region and a random sequence region is utilized. By determining the statistical expectancy of the fixed sequence in the nucleic acid template, this determines the average length of a nucleic acid template that can be sequenced. During the annealing of such a primer with the nucleic acid template, the fixed sequence determines where the complete primer binds by binding to its complementary sequence on the nucleic acid template. The random sequence regions of the primers make it possible for the presence of a unique sequence adjacent to the fixed sequence to be present, thus providing a primer with full complementarity with the nucleic acid template. Thus, this procedure is able to provide a full-length primer with a fully complementary sequence capable of binding statistically once within an expected length of the nucleic acid template, even though the sequence of the template is unknown. The method can also be adopted for use in PCR amplification of a nucleic acid template.

29 Claims, 8 Drawing Sheets

Different fixed sequences in the different degenerate primers

OTHER PUBLICATIONS

Kaczorowski, T. and W. Szybalski, 1994. Assembly of 18-nucleotide primers by ligation of three hexamers: sequencing of large genomes by primer walking. *Anal. Biochem.* 221:127–135.

Kieleczawa, J., et al., 1992. DNA Sequencing by primer walking with strings of contiguous hexamers. *Science* 258:1787–1791.

Kotler, L., et al., 1994. DNA sequencing: modular primers for automated walking. *BioTechniques* 17:554–559.

McCombie, W.R., and Kieleczawa, J., 1994. Automated DNA sequencing using 4-color fluorescent detection of reactions primed with hexamer strings, *Biotechniques* 17:574–9.

Sanger, F. & Coulson, A.R., 1975 *J. Mol. Biol.* 94:444–448.

Senapathy, P. 1986. Origin of eukaryotic introns: A hypothesis, based on codon distribution statistics in genes, and its implications, *Proc. Natl. Acad. Sci. U.S.A.* 83:2133–2137.

Senapathy, P. 1988a Distribution and repetition of sequence elements in eukaryotic DNA: New insights by computer aided statistical analysis *Molecular Genetics (Life Sciences Advances)*, 7:53–65.

Senapathy, P. 1988b. Possible evolution of splice-junction signals in eukaryotic genes from stop codons, *Proc. Natl. Acad. Sci. U.S.A.* 85:1129–1133.

Senapathy, P., et al., 1990. Splice junctions, branch point sites, and exons: Sequence statistics, identification, and applications to the Genome Project, in *Methods in Enzymology, Computer Analysis of Protein and Nucleic Acid Sequences*, Doolittle, R.F., ed., 183:252–278.

Shapiro, M.B. and Senapathy, P., 1987. RNA splice junctions of different classes of eukaryotes: Sequence statistics and functional implications in gene-expression, *Nucleic Acids Research* 15:7155–7176.

Studier, F.W., 1989. A strategy for high-volume sequencing of cosmid DNAs: Random and directed priming with a library of oligonucleotides. *Proc. Natl. Acad. Sci. U.S.A.* 86:6917–6921.

\* cited by examiner

Partly fixed degenerate primer
8 fixed bases    8 random bases

TCTGATCG | NNNNNNNN   (SEQ. ID. NO: 1)

Template DNA sequence (~64 KB)

Partly fixed degenerate primer
5 fixed bases    8 random bases

CAGTG | NNNNNNNN   (SEQ. ID. NO: 2)

Template DNA sequence (~1 KB)

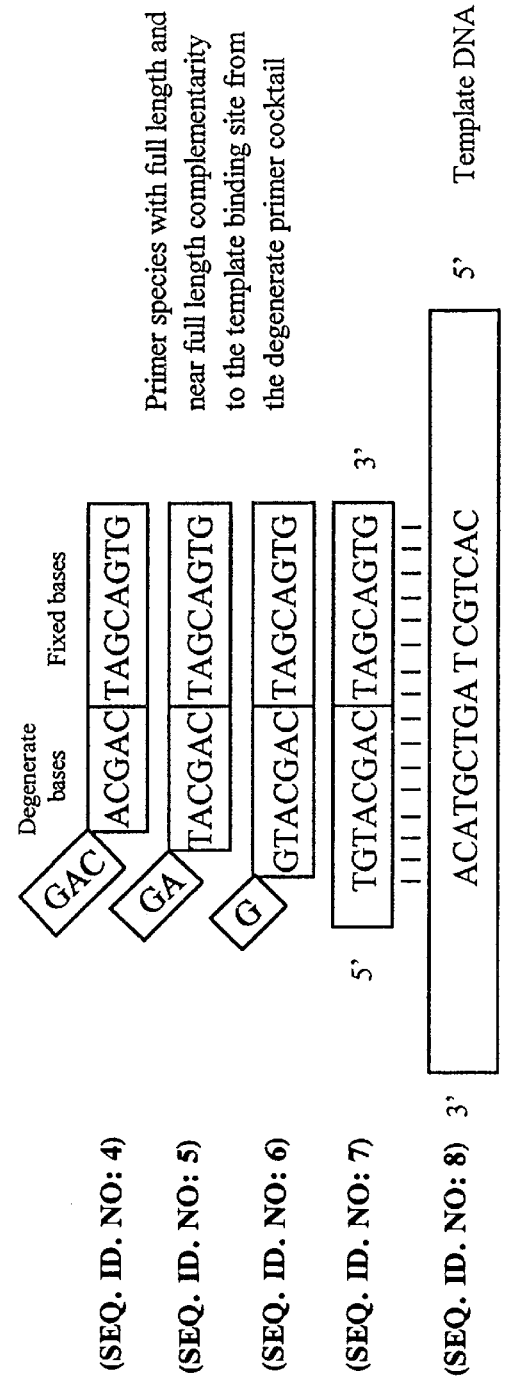

SEQUENCE LISTING

```
<160> NUMBER OF SEQ ID NOS:  7

<210> SEQ ID NO 1
<211> LENGTH: 13
<212> TYPE: DNA
<213> ORGANISM: Artificial Sequence
<220> FEATURE:
<223> OTHER INFORMATION: "n" at positions 6-13 may be A, T, C, or G
<223> OTHER INFORMATION: Description of Artificial Sequence: PCR Primer

<400> SEQUENCE: 1
cagtgnnnnn nnn                                                        13

<210> SEQ ID NO 2
<211> LENGTH: 16
<212> TYPE: DNA
<213> ORGANISM: Artificial Sequence
<220> FEATURE:
<223> OTHER INFORMATION: "n" at positions 9-16 may be A, T, C, or G
```

```
<223> OTHER INFORMATION: Description of Artificial Sequence: PCR Primer

<400> SEQUENCE: 2
tctgatcgnn nnnnnn                                                16

<210> SEQ ID NO 3
<211> LENGTH: 16
<212> TYPE: DNA
<213> ORGANISM: Artificial Sequence
<220> FEATURE:
<223> OTHER INFORMATION: "n" at positions 1-8 may be A, T, C, or G
<223> OTHER INFORMATION: Description of Artificial Sequence: PCR Primer

<400> SEQUENCE: 3
nnnnnnnnta gcagtg                                                16

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence: PCR Primer

<400> SEQUENCE: 4
gacacgacta gcagtg                                                16

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: PCR Primer

<400> SEQUENCE: 5
gatacgacta gcagtg                                                16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: PCR Primer

<400> SEQUENCE: 6
cgtacgacta gcagtg                                                16

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: PCR Primer

<400> SEQUENCE: 7
tgtacgacta gcagtg                                                16
```

US 6,521,428 B1

SHOT-GUN SEQUENCING AND AMPLIFICATION WITHOUT CLONING

Priority is hereby claimed to provisional application Ser. No. 60/130,358, filed Apr. 21, 1999, and incorporated herein by reference.

FIELD OF THE INVENTION

The invention relates to molecular biology methods. In particular, the invention relates to nucleic acid sequencing methods.

REFERENCES TO CITATIONS

A full bibliographic citation of the references cited in this application can be found in the section preceding the claims.

DESCRIPTION OF THE RELATED ART

Billions of DNA bases must be sequenced to meet the goals of the Human Genome Program. Technology must advance so that the amount of bases determined per unit of time is significantly increased, the quality of the data is highly accurate, and the cost per base is significantly decreased. Such technological advancements would enhance large sequencing projects, such as the Human Genome Project, and would benefit other types of research such as discovering and genotyping single nucleotide polymorphisms (SNPs) and gene-based drug discovery.

The current approach used in most large-scale sequencing projects is that of random sequencing of cloned shot-gun DNA fragments. In this procedure, randomly cut, overlapping nucleic acid fragments are cloned to form a library of random clones. These are sequenced. Sequence data from the library is aligned to form contiguous sequences (contigs). An 8–10 fold coverage is required to obtain sufficient overlap matching to obtain a contig. The gaps between the contigs are then filled in using primer-walking. Obtaining the gap sequences (sequences which constitute only the final few percent of the total desired sequence) requires a disproportionate effort compared to the number of nucleotides sequenced within the gaps.

Instead of using shot-gun clones, it would be very advantageous to develop a high-throughput, primer-based DNA sequencing strategy that uses primers selected from a pre-synthesized primer library. Conventional primer-based DNA sequencing requires the synthesis of a vast number of full-length primers for implementing a full-fledged primer-walking procedure. For example, conventional primer walking using 16 base long primers requires the synthesis of $4^{16}$ primers. If a library of shorter primers could be used for this purpose, it would greatly reduce the number of primers needed for primer walking.

In 1989, Studier proposed a strategy for high-volume sequencing of cosmid DNAs using a primer library composed of 8-, 9-, or 10-mers. Others have proposed synthesizing a library containing a subset of useful octamers or nonamers (Slemieniak and Slightom, 1990; Burbelo and ladarola, 1994). The use of ligated or non-ligated pentamer/hexamer strings has also been proposed (Kaczorowski and Szybalski, 1994; Kieleczawa, et al., 1992). A reduced library of selected nonamers has also been proposed (Siemieniak and Slightom, 1990). Several reports have demonstrated limited success with using short primer strings to prime fluorescence-based sequence reactions (Hon and Smith, 1994; Kolter, L., et al., 1994; McCombie and Kieleczawa, 1994)

Bock and Slightom (1995) reported fluorescence-based cycle-sequencing with primers selected from a nonamer library. With the "PRISM"-brand T7 DNA polymerase, a commercial kit available from Perkin Elmer/Applied Biosystems, Inc. (PE/ABI) (Foster City, Calif.), Bock and Slightom reported a complete lack of success. Although reasonable results were obtained using standard oligomers (21-mers), no sequence information was generated with nonamer primers (using the same template DNA) even after testing several different template and nonamer concentrations. Bock and Slightom used the PE/ABI cycling sequencing procedure, which gave some weak results. However, even after optimizing reaction conditions for sequencing to suit the nonamers, this procedure had a success rate of only about 50%. The modified PE/ABI cycle-sequencing procedure contained some very unusual steps. For example, the use of linear and pre-denatured plasmid DNA was a must even for this low success rate. Other peculiarities associated with the procedure included the use of a low annealing temperature (20° C. for 5 min) followed by a 5-min ramp to the 60° C. extension temperature and the use of 50 cycles. According to the authors themselves, this level of success is somewhat disappointing, as they have only partially satisfied the goal of a primer library-based DNA sequencing strategy. Thus, additional improvements are needed before such a strategy can be considered practical for large-scale genome-type sequencing.

In addition to the nonamer-based cycle-sequencing method, both (1) Hardin, et al., (1996) and (2) Jones and Hardin (1998) made efforts at carrying out octamer-primed cycle-sequencing. However, as in the case of the nonamer, this is not effective for large-scale sequencing. When octamers from a 50% GC library were assayed, only five out of fourteen primers produced sequence information, resulting in an unacceptable 35.7% reaction success rate. Optimized conditions had to be used for sequencing a particular DNA template, and a set of optimized, 75% GC library had to be selected, which gave a success rate of ~73%. For this success rate, a low annealing temperature of 40° C. had to be employed, and the reaction had to be cycled for 99 rounds (instead of the usual 30 cycles). Ball, et al., (1998) have extended the use of octamer primer by tailing the primers with modified bases. The authors used, among other modified bases, 5-nitroindole in a tail, which was expected to stabilize the primers while behaving indiscriminately in base-pairing. Although this process improves the signal intensity, there were limitations. For example, only a maximum of four 5-nitroindole residues could be added. Longer tails (>6 residues) were detrimental, as they loop back on themselves, destabilizing the primer. Additionally, longer runs of 5-nitroindole residues can form secondary structures. The optimum length for the 5-nitroindole tail is 3–4 residues. This study also showed that a considerable percentage of cases required the addition of a tail to an octamer for obtaining any sequence data. A very low annealing temperature of 30° C. had to be used.

While these studies indicated that shorter oligonucleotides such as nonamer or octamer could be used for sequencing for some situations, it is clear that these approaches have severe limitations. It will be very advantageous to developing a method by which considerably longer oligonucleotides can be provided as primers, and yet the ease of availability of primers is not compromised. What is needed is a method using longer, full-length primers for cycle-sequencing when little or no sequence information of template DNA is available. What is also needed is a method using the longer, full-length primers in combination with both (1) shot-gun sequencing for obtaining the majority of the sequence and (2) primer walking for closing the gaps. This method should avoid random fragmenting and sub-cloning the DNA and avoid the need for preparing new full-length primers.

SUMMARY OF THE INVENTION

The present invention utilizes primers in which a region of the primer sequence is fixed, and, in the preferred embodiment, the remainder of the primer sequence is randomized, thereby providing an array of all the possible sequences. Accordingly, a full-length primer species will be available to bind to a particular sequence in the template DNA.

It is a principal aim of the present invention to provide a method for sequencing a long DNA molecule without fragmenting or sub-cloning the long DNA molecule.

It is a further aim of the present invention to provide a method for PCR amplifying a DNA fragment with a long-fixed sequence degenerate primer and a short-fixed sequence degenerate primer.

Yet a further aim of the present invention is to provide a method for sequencing a long DNA molecule with a primer having an arbitrary sequence handle. The handle improves the sequencing reaction.

Yet a further aim of the present invention is to provide a method for amplifying a long DNA molecule with a primer having an arbitrary sequence handle. The handle improves the amplification reaction.

The invention is directed to a method of sequencing a nucleic acid template. The method comprises the steps of: (a) providing a plurality of first primers, each first primer comprising (i) a region of fixed nucleotide sequence and (ii) a region of randomized nucleotide sequence located 5' to, 3' to, flanking, or interspersed within the region of fixed nucleotide sequence; and then (b) annealing the first plurality to a nucleic acid template, wherein at least one primer anneals to the template. The annealed first primer is then (c) extended with a mixture of dNTPs and ddNTPs to generate a series of nucleic acid fragments. The nucleotide sequence of a first region of the template is then (d) determined from the series of nucleic acid fragments.

In the preferred embodiment, the invention further comprises the steps of providing a plurality of second primers, each second primer also comprising (i) a region of fixed nucleotide sequence and (ii) a region of random nucleotide sequence located 5' to, 3' to, flanking, or within the region of fixed nucleotide sequence. Steps (b)–(d), above, are then repeated for the second plurality of primers to thereby determine the nucleotide sequence of a second region of the template. The first sequenced region and the second sequenced region of the template nucleic acid are then assembled to form a first contig. These steps can then be repeated ad infinitum to form additional contigs.

Sequence gaps between contigs can the be determined by providing a plurality of third primers, each third primer comprising (i) a region of fixed nucleotide sequence and (ii) a region of random nucleotide sequence located 5' to, 3' to, flanking, or within the region of fixed nucleotide sequence and annealing the plurality of third primers to the nucleic acid template, wherein at least one primer from the third plurality anneals to the template near a terminus of one of the first or second contigs. The annealed third primer is then extended with a mixture of dNTPs and ddNTPs to generate a series of nucleic acid fragments. The sequence of the template between the first and second contigs is then determined from the series of nucleic acid fragments.

The process of the invention can be repeated as often as desired to sequence the entire length of the target nucleic acid molecule.

The invention is further drawn to a method for amplifying (as opposed to sequencing) a nucleic acid template. Here, the method comprises providing a plurality of first primers, each first primer comprising (i) a region of fixed nucleotide sequence and (ii) a region of randomized nucleotide sequence located 5' to, 3' to, flanking, or within the region of fixed nucleotide sequence; providing a plurality of second primers, each second primer comprising (i) a region of fixed nucleotide sequence and (ii) a region of randomized nucleotide sequence located 5' to, 3' to, flanking, or within the region of fixed nucleotide sequences, wherein the region of fixed nucleotide sequence of the second plurality of primers is shorter than the region of fixed nucleotide sequence of the first plurality of primers; and then amplifying the nucleic acid template with the first and second plurality of primers, wherein at least one primer from the first and second plurality anneals to the template.

Further aims, objects, and advantages of the invention will become apparent upon a complete reading of the Detailed Description that follows.

BRIEF DESCRIPTION OF THE DRAWINGS

FIGS. 3A and 3B are schematics showing a 5-base fixed-sequence region primer (A), and the individual primers from the degenerate primer mixture with full-length and near full-length complementarity to the template binding site.

DETAILED DESCRIPTION OF THE INVENTION

In the present invention, a primer of partly-fixed sequence is used as a sequencing primer. This partly-fixed sequence primer has (i) a region of fixed nucleotide sequence and (ii) a region of randomized nucleotide sequence located 5' to, 3' to, flanking, or within the region of fixed nucleotide sequence. Such primers and a method of using a primer of partially fixed sequence are the subject matter of approved patent application Ser. No. 08/406,545 now U.S. Pat. No. 5,994,058, issued Nov. 30, 1999 to the subject inventor, the entirety of which is incorporated herein. The partially-fixed primer is comprised of a fixed-sequence region of a defined length, and a random sequence region. The overall sequencing approach described herein in conjunction with the invention is a cycle-sequencing protocol. This is done solely to illustrate the invention, not to limit it. Other sequencing approaches, such as traditional non-cycle-sequencing, can also be used with equal success. The invention is described herein as sequencing or amplifying a DNA template. Likewise, this is done solely to illustrate the invention, not to limit it. Any other nucleic acid template, such as a cDNA molecule or an RNA molecule, can be used as template with equal success. DNA templates can be in various forms, such as genomic DNA, PCR products, and the like. In short, neither the nucleic acid template itself nor the origin of the nucleic acid template (natural, synthetic, source organism) are critical to the functionality of the invention.

Figure 1:
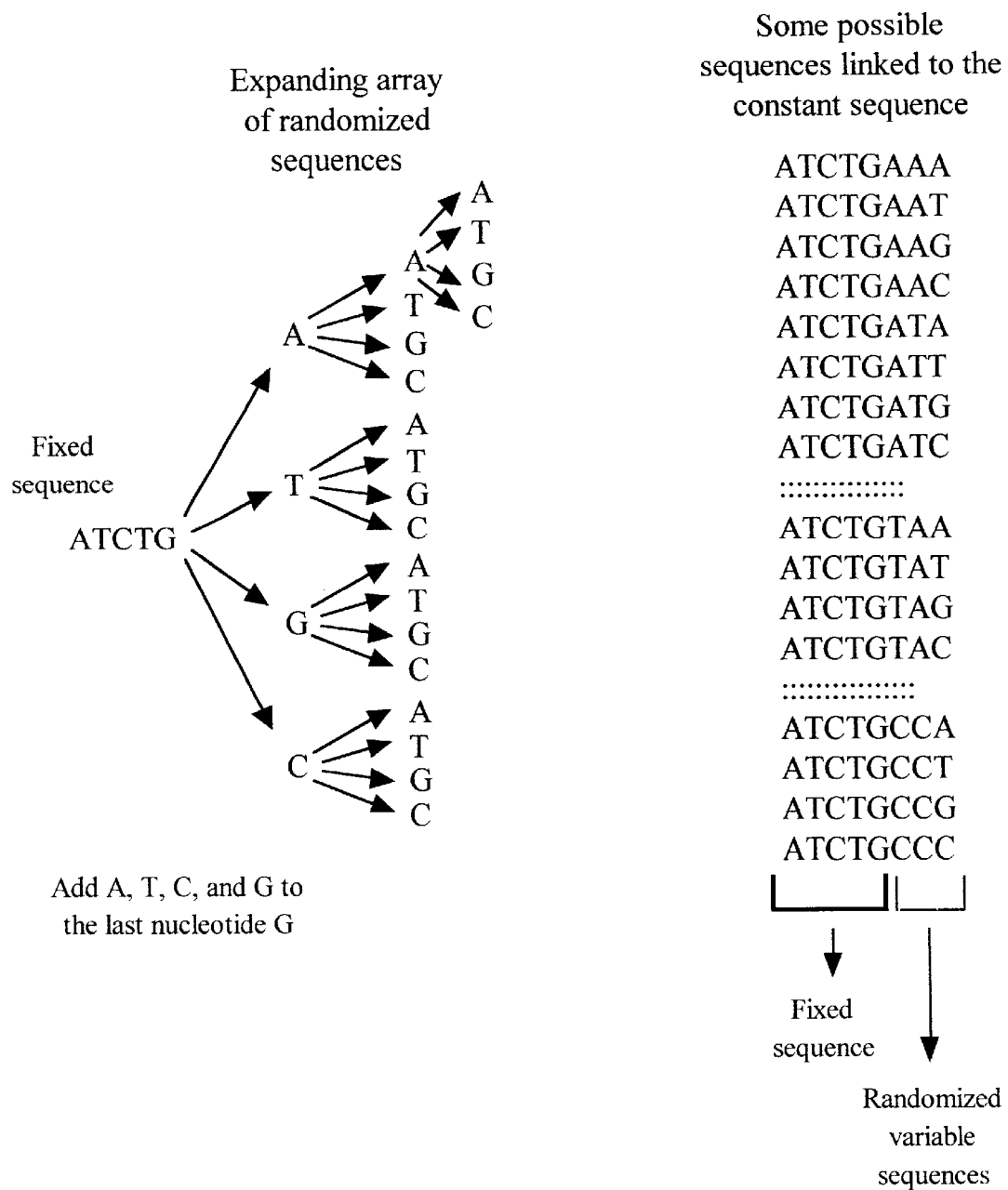
FIG. 1 is a schematic of the array of primer created with the invention.

Referring to FIG. 1, an important concept of the present invention is that by adding randomized nucleotides to any target sequence of less-than-optimum primer length, the primer cocktail will then contain a large plurality of full-length primers, each of which primer includes the target sequence within it. Each individual primer species within the primer cocktail is a full-length primer, with the capability of binding with standard complementarity at a specific location within a DNA sample which exhibits the target sequence. Because biologically-derived DNA has random sequence characteristics, it lends itself to such random sequence manipulation (Senapathy, 1986; Senapathy, 1988a; Senapathy, 1988b; Senapathy, et al., 1990). Depending upon the number of randomized bases added to the target fixed sequence, an increased concentration of the primer or subset of primers can be used to increase the mole equivalent of a particular primer species to that of the primer concentration normally used in standard sequencing or PCR reaction.

Figure 2A:
FIGS. 2A and 2B are schematics showing full complementarity for a 5-base fixed-sequence region primer in a 1 kb template (A) and an 8-base fixed-sequence region primer in a 64 kb template (B).
Figure 2B:

In a partly-fixed primer sequence, a given length of the sequence has a fixed sequence, and the rest of the nucleotide positions within the primer have all the four nucleotides randomized at each of the positions. Such a primer preparation will have all the possible sequences at the degenerate positions. Adjacent to the location where the fixed sequence region of the primer binds with full complementarity on the template DNA, one of the primer species will also have full complementarity in the randomized region of the primer. Therefore, in the degenerate primer preparation, there will be one species of primer that will have full complementarity at the primer binding location, which is determined by the fixed sequence in the degenerate primer. These degenerate primers are diagrammed in FIGS. 2A and 2B. FIG. 2A shows a degenerate primer with 5 fixed bases and 8 randomized bases. This primer binds once with full complementarity to a binding site in a 1 kb template. This is because the waiting-interval for a 5 base sequence is $1/4^5 = 1,024$ bases. FIG. 2B shows a degenerate primer with 8 fixed bases and 8 randomized bases. This primer binds once with full complementarity to a binding site in a 64 kb template (i.e., the waiting interval for an 8 base sequence is $1/4^8 = 65,536$).

In general, as originally described by Sanger and Coulson (1975), DNA sequencing is currently done by annealing a primer to a template, extending the primer with a mixture of deoxynucleotides (dNTPs) and di-deoxynucleotides (ddNTPs) to generate a series of DNA fragments. The sequence of the template is determined from the DNA fragments. Typically the sequence is determined by running the fragments on a gel or through a capillary that can separate the DNA fragments at one-base intervals. Traditionally, a primer is chosen based on the known sequence of the template.

A method is presented for sequencing an unknown DNA of a given length, (e.g., 10–100 kilobases (kb)), without fragmenting and sub-cloning as in conventional random shot-gun sequencing procedure, or without requiring fully-known primers as in conventional primer-walking procedures. This method uses the knowledge that a degenerate primer with a given number of fixed nucleotides will statistically occur only once within a template DNA of a particular length. The number of fixed nucleotides in the degenerate primer statistically determines this template DNA fragment-length. For example, if the partly-fixed degenerate primer occurs only once in the template DNA of approximately 10–20 kb in length, this primer can be used to sequence about 500 bases at an undetermined location within the template DNA. Although many different species of primer sequences will occur in the degenerate primer preparation, only one of them will have a fully-complementary sequence to the primer-binding site on the template DNA. Therefore, only one of the primer species, whose binding location is determined by the fixed sequence in the degenerate primer, is expected to bind to the template DNA at a standard stringent temperature of annealing. Because the fixed sequence occurs only once in the template, this primer species is not expected to bind anywhere else. The lengths of both the fixed-sequence region in the degenerate primer and the DNA molecule to be sequenced can be adjusted in such a manner that the fixed sequence will match with a corresponding complementary sequence approximately once in the DNA molecule.

Cycle sequencing is generally carried out at a slightly lower annealing temperature of from about 50° C. to about 52° C. for sequencing primers having a $T_m$ of from about 55° C. to about 65° C. This range of annealing temperatures is generally considered to be optimum for cycle sequencing. Also, in cycle sequencing reactions, up to about 20% non-specific binding and generation of non-specific fragments are tolerated, meaning that these non-specific products do not interfere with the generation of readable sequencing patterns. Therefore, in addition to the primer species that has fully complementarily binding, primer species with one or a few mismatches may also bind specifically enough. These mismatched primer species that are bound at the primer-binding site also produce correct cycle-sequencing fragments. See FIGS. 3A and 3B for mismatches at the farthest 5' end of the primers. In essence, the fixed sequence anchors the primer on the template DNA specifically at its complementary sequence. The randomized degenerate region provides one full-length primer species and many near full-length primer species that bind to complementary flanking sequences. Thus, a longer specific sequence binds at that site, providing a longer length specific primer for the priming reaction.

By using many degenerate primers, each with a different fixed sequence, many different approximately 500 base sequences can be obtained from different regions on the template DNA, where each of the different fixed sequences within the degenerate primer bind specifically. The simultaneous sequencing of template DNA, with many different degenerate primers with different fixed sequences, can form a few contigs.

For closing the gaps between the contigs, one can then apply a directed primer walking method using fully known primers or the fixed sequences of degenerate primers that occur near the ends of the contigs. This method is therefore highly advantageous for completely sequencing a template DNA without fragmenting and sub-cloning the DNA. It is also advantageous over the conventional primer-walking method, because it avoids the preparation of a large number of full-length primers. It only takes a set of a few different degenerate primers having different fixed sequences that can be prepared in bulk. This set (wherein the overall plurality of primers includes primers having different fixed sequences) can be used for any given template DNA of approximately 8–10 kb in length. Also, this method is capable of avoiding the 10-fold sequencing of the template DNA that is usually required in the conventional shot-gun sequencing method.

Furthermore, template DNA fragments of an approximate length, such that a fixed sequence within a degenerate primer occurs only once, are used. This template DNA fragment can vary from ~1 kb to ~1 MB or longer, depending upon the limitation in the upper length-limit of any template DNA that can be cycle sequenced. This limitation may be overcome as described below.

Primers can also be designed such that longer fixed sequences are included in the degenerate primer. For example, fixed sequences of 4–25 bases, and more preferably 10–12 bases, are used. Also, sequences that occur more frequently than would be expected based on a random distribution of nucleotides in a given template DNA can be used as fixed region of the degenerate primer. Thus, even longer fixed sequences can be designed such that they occur only once within shorter lengths of template DNA.

Cycle-sequencing a Template DNA Using a Degenerate Primer Containing a Fixed-sequence The purpose of the current invention is to provide a full-length primer with a capability to bind with specific complementarity at one location on a template DNA whose sequence is unknown. Where this occurs, then cycle-sequencing can be carried out from this specific, single binding site. This is achieved by providing a degenerate primer containing a fixed sequence region and a randomized sequence region. The fixed sequence region determines the average length of a random DNA sequence in which the fixed-sequence region is statistically expected to occur once. If L is the number of fixed nucleotides within a degenerate primer sequence, $4^L$ is the length of the random sequence in which the fixed sequence would statistically occur once. For example, if L=2, then the fixed sequence would statistically occur once in every $4^2$ (or 16) bases.

The randomized sequence region of the degenerate primer is prepared in a manner such that each of all the four nucleotides is sequentially added at each position of the randomized sequence linked to the fixed nucleotide sequence. If R is the number of randomized nucleotides and R=2, then there would be $4^2$ (or 16) different combinations of the random nucleotides when R=2, then the following additions would occur: AA, AT, AC, AG, TA, TT, TC, TG, CA, CT,CC, CG, GA, GT, GC, and GG. This process permits an exponential array of all the possible random sequences to be generated during the synthesis, each of which is linked to the fixed sequence. See FIG. 1. This exponential linking or addition of all the four nucleotides, Ns, to the immediately previous nucleotides, makes it possible for any given sequence of the length of the total number of Ns to be present in the primer preparation. Thus, all possible randomized Ns would be available for binding at its complementary sequence on a given template DNA at the site of binding of the fixed-sequence region of the primer.

During the annealing of such a primer with a template DNA, the fixed sequence determines where the complete primer binds by binding to its complementary sequence on the template DNA. The randomized sequence arrays make it possible for the presence of a unique sequence adjacent to the fixed sequence in the primer to be present with full complementarity on the template DNA at the site of the fixed-sequence binding. Thus, this procedure is able to provide a full-length primer with complementary sequence capable of binding statistically once within an expected length of a template DNA, although the sequence of the template DNA is unknown.

By this procedure, the new invention enables the cycle-sequencing of a template DNA of a given length using degenerate primers with partly-fixed sequences. For example, with a degenerate primer of approximately 16–20 nucleotides length in which 7 bases are fixed, and the remaining bases are randomized, a 10 kb template DNA can be sequenced. From a statistical standpoint, one of the different 7-fixed sequence degenerate primers will occur once at a random position within the 10 kb DNA.

Figure 4:
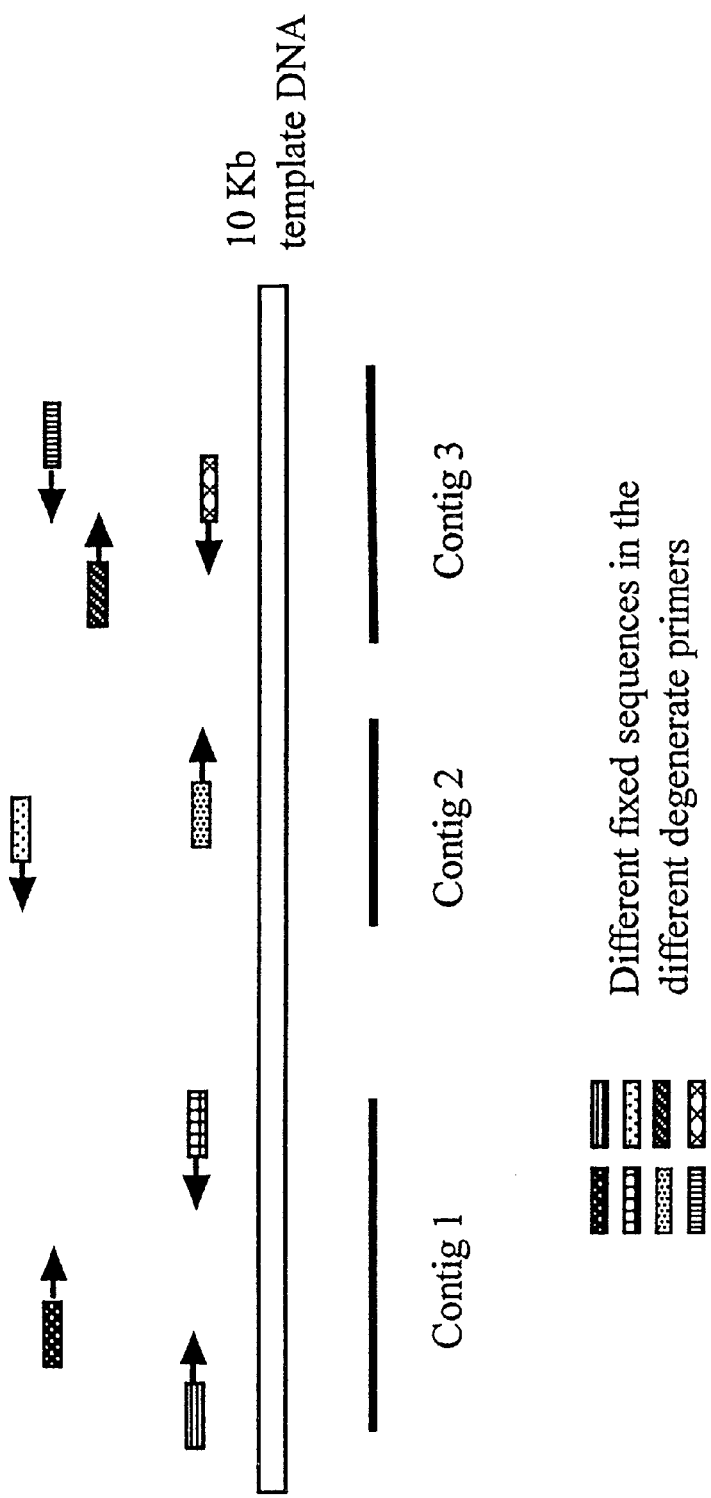
FIG. 4 is a schematic showing the contig formnation from sequence data derived from cycle-sequencing using degenerate primers.

A sequence of about 500 bases can be obtained using this primer as the cycle-sequencing primer. Similarly, different primers with different 7-base fixed-sequence region primer will allow the sequencing of the 10 kb DNA at different, random positions, resulting in contigs, as is shown in FIG. 4.

The probability of a given 7-base sequence occurring in a template DNA is $1/4^7$, which is once in 16,384 bases. It can be expected that, on average, a given 7-base sequence will occur approximately once within the 16 kb DNA. The reason is that the waiting interval (i.e., the distance between two events) between the successive repetitions of particular oligonucleotide sequence in a random DNA is distributed in a negative exponential manner (Senapathy, 1986; Shapiro and Senapathy, 1987; Senapathy, 1988a; Senapathy, 1988b; Senapathy, et al., 1990).

Approximately 70% of successive repetitions of a particular sequence occur at shorter than the mean waiting-interval. Thus, if we mix a given 16 kb DNA template with any given 7-base fixed-sequence region primer, it can be expected to have about one binding site in the DNA. This is because the probability of occurrence of a given 7-base fixed-sequence region primer within a DNA of ~16 kb is 0.7. See Senapathy, P., 1988a. However, for a successful priming at a stringent temperature, a primer must be approximately 15 bases or longer. So, we can use a partly-fixed degenerate sequence, in which only 7 bases are fixed, and the rest are randomized bases for this purpose. There will be a species of primer that will bind specifically at that particular site at a standard stringent temperature. Thus, at the stringent temperature, this primer species can be used for cycle-sequencing.

The procedure outlined above can be repeated with another degenerate primer with a different 7-base fixed region sequence in the primer. This primer will bind at a different site, anywhere within the template DNA where the complementary sequence to that 7-base fixed region occurs. Referring to FIG. 4, therefore, another 500 base sequence can be obtained by cycle-sequencing. The repetition of this procedure will generate, every time, a sequence of approximately different 500 bases. Thus, to fill in the sequence between the contigs, a regular primer-walking can be carried out using degenerate primers with fixed sequence regions by using fixed sequences that occur at or near the end of a sequenced region.

The sequencing of a template DNA with many degenerate primers with different 7-base fixed-sequence region can be simultaneously carried out. Because the locations of these primers may occur anywhere within the 10 kb template DNA, this approach will produce sequences akin to a conventional random shot-gun approach, except that the DNA is not fragmented and sub-cloned. Furthermore, because this process is preferably done only to obtain a few contigs, and not to completion, the 8 to 10-fold excess sequencing done in conventional shot-gun sequencing is avoided.

Figure 5:
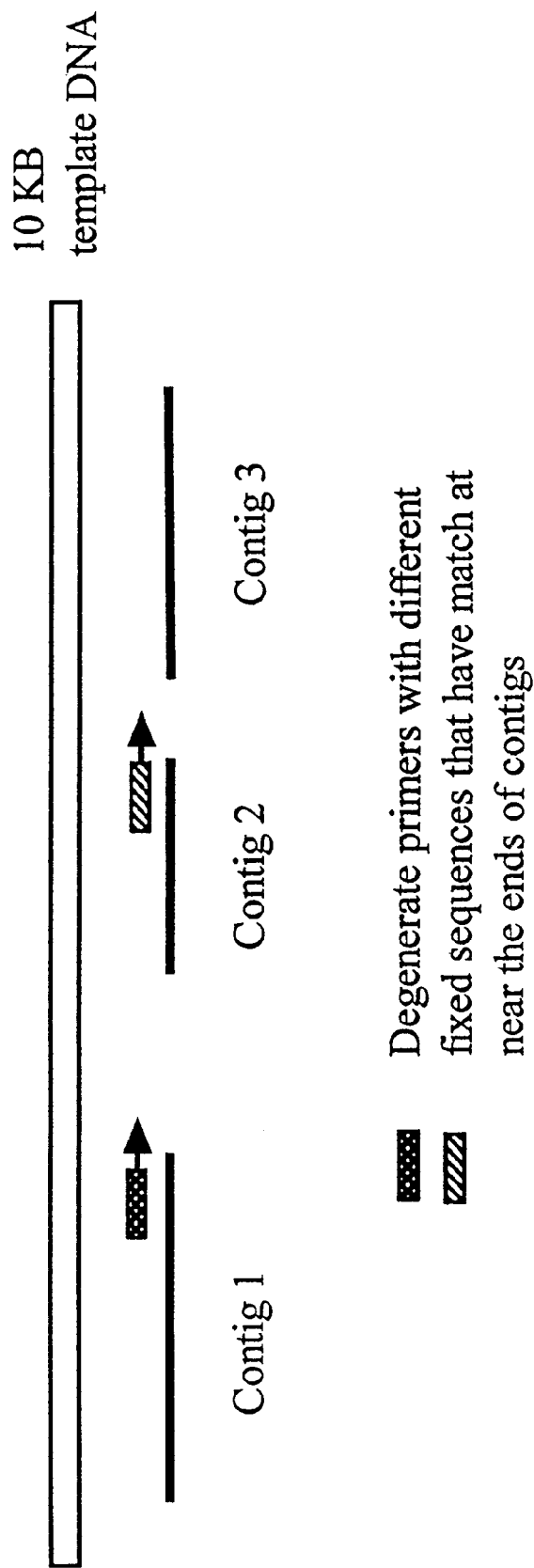
FIG. 5 is a schematic showing the closing of the gaps between contigs of FIG. 4 using degenerate primers with fixed sequences that match near the ends of the contigs.

As is shown in FIG. 5. and described below, the gaps between the contigs can be determined using primers having a fixed region of 7 nucleotides long near the ends of the contigs, from an available set of given primers. Thus, this procedure is able to sequence a complete 10 kb DNA with only a small set of degenerate primers with different fixed sequences. The same set of degenerate primers can be essentially used to sequence any 10 kb DNA template.

The Need for a Small set of Degenerate Primers for Sequencing a DNA Template

There is another advantage to the current invention. In a genomic sequencing procedure, two-fold sequencing is desired for verifying the sequence. In the conventional shot-gun approach, it is achieved because the sequencing is carried out approximately 8–10 fold, with finally filling in the gaps by primer-walking. In the regular primer-walking procedure, again it has to be sequenced once more with new primers. That means, it would take ~20 new primers for cycle-sequencing a 10 kb DNA template in one pass and approximately 40 new primers for two passes of sequencing. In the current invention, it would take only a set of about 40–50 degenerate primers for two passes for sequencing a given 10 kb DNA that can be chosen from a larger master set of about 200 primers. About the same number of degenerate primers (~50) would be needed for sequencing any given 10 kb DNA, which can be selected from the same master set again. This set of degenerate primers can be prepared in bulk. The repeated use of the same master set of about 200 degenerate primers for sequencing any given 10–20 kb DNA is very advantageous over both the conventional methods of sequencing.

Closing the Gaps Between Contigs with the Same Set of partly-fixed Degenerate Primers:

The invention also provides a method for closing the gaps between contigs using degenerate primers. Optionally, a pre-made master set of degenerate primers can be generated. Once a few contigs are formed, the end of each contig can be searched to determine if any one of the set of degenerate primers is present within the sequence near the end of the contig, as is shown in FIG. 5. If one is present, then a degenerate primer with this fixed-sequence can be used to obtain a sequence of additional 500 bases from this location without preparing a new full-length primer. Because there is no need to find a primer at a specified, exact nucleotide site towards the end of the contig, the probability of finding a degenerate primer fixed sequence somewhere near the end of a contig is high, and makes it practically feasible to implement this strategy.

By employing a set of about 100 or 200 different degenerate primers with a different fixed-base sequence in each of them, it is possible to find a sequence that matches with one of these fixed-sequences at near the end of any given contig. Consider the frequency of a given 6-base fixed-sequence. The average length of DNA sequence in which a given 6-base fixed-sequence will occur once is $4^6$ bases (4096 bases). Thus, with a set of 100 different 6-base fixed-sequence region primers, the average length in which any one of these will be expected to occur once is approximately 40 bases (i.e., 4096 bases/100). Thus, with a set of only 100 degenerate primers each with a different 6-base fixed sequence, any gap between contigs can be sequenced. With a 7-base fixed-sequence region primer, the number of possible sequences is $4^7=16,000$. Thus, with 300 different 7-base fixed-sequence region primers, any one of these can be found approximately within 16,000/300=53 bases near the 3' end of the contig. Furthermore, the same set of degenerate primers can be used repeatedly for sequencing any number of different template DNA molecules.

Using this basic principle, one can also primer-walk contiguously from a known sequence end. This is done by searching for the presence of a primer's fixed part near the 3' end of the contig. This process eliminates the need for preparing new full-length primers, thus saving the cost, time, and labor used, and simultaneously the required primers are readily available.

Thus, an advantage of this method, even for closing gaps between contigs, is that specific full-length primers do not have to be prepared. On the whole, therefore, a given DNA of approximately 10–20 kb can be sequenced without preparing any specific full-length primers. Thus, an advantage of the current invention is that it avoids the need for preparing full-length primers for primer walking. In the conventional primer-walking procedure, for each walk a new primer must be made based on the newly sequenced DNA region. In contrast, in the new invention, the same set of about 20–30 different primers with different 7-base fixed degenerate primers can be used repeatedly for any given 10 kb fragment. Referring to FIG. 5, in addition, after a few contigs are formed by repeating the steps which leaves a few gaps, regular primer walking using a few other degenerate primers can be used for closing the gaps. For sequencing a 10 kb DNA fragment with conventional shot-gun sequencing, it would take approximately 10,000 bases/500 base=20×10=200 shot-gun sequencing reactions. However, it would only take approximately 20 random primer reactions with the degenerate primers from a pre-made set of about 200 primers. It would only take approximately additional 3–5 directed walks using degenerate primers from the same set of degenerate primers for closing the gaps. Thus, significant advantages are realized over both the conventional shot-gun approach and conventional primer-walking methods. For example, the inventive method avoids the random fragmentation and sub-cloning of DNA fragments. The inventive method also avoids a significant number of sequencing reactions required in the conventional shot-gun approach. Still further, the inventive method avoids the preparation of a large number of full-length primers as required in the conventional primer walking method. Thus, the current invention has many advantages over both the conventional shot-gun sequencing method and the conventional full-length primer walking method.

The above discussion with 6- or 7-base fixed-sequence region only exemplifies the invention; the invention is not limited to primers having a 6- or 7-base fixed-sequence region. The fixed sequence can vary considerably in the degenerate primer. A fixed sequence from a minimum of 3-bases can be used. There is no upper limit to the length of the fixed-sequence region (or the overall length of the primers). Preferably, however, the fixed region should be no more than about 40 nucleotides.

Using the Predicted $T_m$ of a Degenerate Primer in Cycle-sequencing a Specific Template DNA As described above, a degenerate primer is actually a mixture of an exponential array of different primers. The $T_m$ of the different primers within a degenerate primer mixture that actually bind a given template can be determined. At least a portion of a given template is searched for the presence of the fixed region of the degenerate primer. A portion of a given template fairly represents the rest of the template. Thus, results generated in the search are applicable to the entire template. When the fixed portion is found in the template, additional bases are added on either side (or both sides) to produce the full binding site. The $T_m$ of the full binding site is determined using a method known to the art. For example, the $T_m$ can be calculated with the following simple equation: every A and T=2° C., and every C and G=4° C. The $T_m$ of several binding sites is determined, and the frequency of the various $T_m$s is calculated. If the $T_m$s of the different primers within a degenerate primer occur over a narrow range, a more efficient binding reaction will occur at a given temperature compared to when the $T_m$s of the different primers within a degenerate primer occur over a wide range. Thus, it is advantageous to know the $T_m$ of a degenerate primer species in a PCR reaction or a cycle-sequencing reaction. This ability permits a more precise design of the degenerate primer's temperature of annealing.

The Occurrence and Advantage of Longer Fixed-sequence Degenerate Primers in a Template DNA In another embodiment of the invention, it has been observed that some oligonucleotides occur at a higher frequency in a given genomic DNA than would be expected for a random DNA sequence. It should be noted that some other primers occur at a lower frequency in a given genomic DNA than expected for a random DNA sequence. The distribution of these oligonucleotides in the genomic DNA is generally uniform without much bias in different regions of the DNA. Thus, if the distribution of an oligonucleotide is determined for a portion of the template, this determination is applicable to the entire template. Applying these observations, it can be seen that some longer fixed sequence will occur at about the same frequency as that of a shorter fixed sequence. Referring to Tables 1 and 2 below, the probability of a 5-base fixed-sequence region primer occurring is once in a 1 kb template DNA. Therefore, on average a degenerate primer with a 5-base fixed-sequence region will occur once in one kb of DNA. Normally, an 8-base fixed-sequence region primer will occur once in 64 kb (65,536 bases). If, however, an 8-base fixed-sequence region primer occurs at a 64-fold more frequent rate in a genomic DNA, it will occur, on average, once in 1 kb of DNA (i.e., 65,536 bases/64=1 kb). Therefore, the frequency of occurrences of both of these primers is the same.

To illustrate this embodiment of the invention, consider a 10-base fixed sequence. Its expected frequency of occurrence in a random DNA is $4^{-10}$, and the mean expected occurrence is one in approximately one million bases in a random DNA sequence. However, if it occurs at a frequency that is 64-times higher than its expected frequency, it would occur once in ~1,000,000/64=~16,000 bases. This is the same as the expected frequency for a 7-base fixed sequence. Therefore, we can now use this 10-base fixed sequence that occurs at a 64-times higher frequency than expected, as if it is a 7-base fixed sequence in a random DNA sequence. A degenerate primer with a longer fixed-sequence is more beneficial than a shorter fixed-sequence in a PCR reaction (or a cycle-sequencing reaction) because the $T_m$ ranges of the 10-base fixed-sequence region primer will be narrower than the 7-base fixed-sequence region primer. Thus, there is better control over the $T_m$ of the degenerate primer. Because a 10-base fixed-sequence region primer has less random bases than a 7-base fixed-sequence region primer, less primer is needed to obtain a mole to mole equivalence of the single primer species that would bind at the primer-binding site.

Cycle-sequencing with More Frequently Occurring Long Oligonucleotide Sequences in a Template DNA Generally, cycle-sequencing is carried out with primers that are 15 bases or longer. The conventional assumption is that shorter primers will non-specifically bind with a template DNA or will not bind even at the specific binding site at stringent temperatures. However, with sufficient precision, there should be a temperature at which a short primer (e.g., 7-base length) may bind to a template DNA only at the specific location where its complementary sequence occurs. The important requirement is that the template DNA length should be such that the primer sequence occurs only once in it. As noted above, some oligo-sequences may occur far more frequently (or less frequently) in a template DNA than is expected. This provides a longer-sequence primer that occurs only once in a template DNA. The following is a table of the fixed-sequence region length and the length of the template DNA in which it is expected to occur once. For example, as Table 1 shows, an 8-base fixed-sequence region sequence occurs once on average in a 64 kb DNA (65,536 bases).

TABLE 1

Expected length of template DNA for n-base fixed-sequence region to occur once (4ⁿ)

| Oligonucleotide Length | Length of Template DNA |
| --- | --- |
| 5-base fixed-sequence region | 1 kb (1,024 bases) |
| 6-base fixed-sequence region | 4 kb (4,096 bases) |
| 7-base fixed-sequence region | 16 kb (16,384 bases) |
| 8-base fixed-sequence region | 64 kb (65,536 bases) |
| 9-base fixed-sequence region | 256 kb (262,144 bases) |
| 10-base fixed-sequence region | 1024 kb (1,048,576 bases) |

As is shown below in Table 2, if an 8-base fixed-sequence region, which normally binds every 64 kb, occurs at a 64-fold higher frequency than expected, then on average it occurs once in a 1 kb template DNA. Therefore, this 8-base fixed-sequence degenerate primer can be used as a primer to cycle sequence at this site of the particular template DNA that is ~1 kb in length.

TABLE 2

Expected length of template DNA for 64-fold higher frequent n-base fixed-sequence region to occur once (4ⁿ)

| Oligonucleotide Length | Length of Template DNA |
| --- | --- |
| 8-base fixed-sequence region | 1 kb (1,024 bases) |
| 9-base fixed-sequence region | 4 kb (4,096 bases) |
| 10-base fixed-sequence region | 16 kb (16,384 bases) |
| 11-base fixed-sequence region | 64 kb (65,536 bases) |
| 12-base fixed-sequence region | 256 kb (262,144 bases) |
| 13-base fixed-sequence region | 1024 kb (1,048,576 bases) |

These highly frequent n-mer sequences can be used as the fixed part of the degenerate primers. Thus, a 8-base fixed-sequence region primer (where this primer occurs 64-fold more frequently in a template DNA) can be used to bind once in a 1 kb DNA fragment, either for PCR or for cycle-sequencing.

As was discovered, some of the 10-base fixed-sequence region primers occur at a 100-fold more frequency in biological DNA. This means that one can use a 10-base fixed-sequence region primer instead of a 7-base fixed-sequence region primer in a degenerate primer and expect this to occur once in about 16 kb, instead of once in a million bases. An 11-base fixed-sequence region primer that occurs at a 100-fold more frequency can be expected to occur once in 64,000 bases, instead of once in 4 million bases.

Optional Pre-amplification Before Cycle-sequencing

A template can first be PCR amplified using a longer-fixed sequence degenerate primer as the first primer and a shorter-fixed sequence degenerate primer as the second primer. Typically, only a few cycles of PCR is needed, but can be varied depending on the amount of starting template and/or the desired amount of PCR product. Once the template is amplified, it can be cycle sequenced. This would ensure that there is sufficient template DNA, especially in cases where the starting quantity of template DNA is relatively low. Optionally, the longer-fixed sequence primer can be labeled, for example, with a fluorescent dye such that DNA sequencing fragments will be labeled.

Uniformity Index for Highly Frequent Primers

Figure 6:
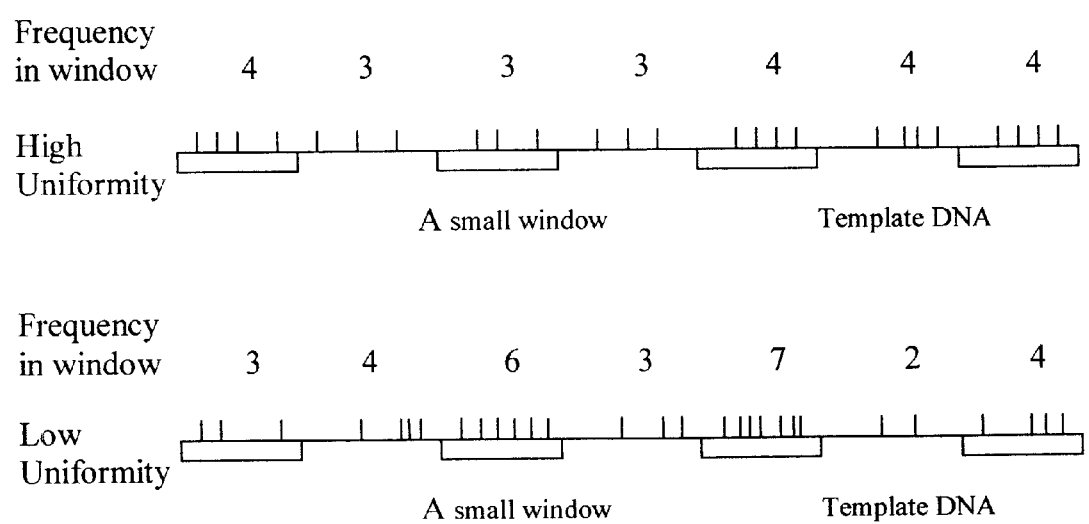
FIG. 6 is a schematic of a primer having a high uniformity index and a primer having a low uniformity index.

Some oligonucleotides may occur more uniformly than others may. If the template DNA sequence is known, then the frequency of a given oligonucleotide sequence within the template DNA can be determined using a computer. The frequencies of each of all the possible sequences of a particular length can be computed, and the sequences can be sorted on the frequencies. From this, a degenerate primer with a particular fixed sequence that occurs at a desired frequency can be chosen. Thus, for some applications a more advantageous process is to select primers that occur more frequently and also more uniformly in a template DNA. By processing a given oligonucleotide for its frequency within small windows within a template DNA, and by assessing the uniformity of the frequencies within different windows, one can ascribe a uniformity index, as is shown in FIG. 6. If the frequency of the particular oligonucleotide in more windows occurs closer to an average frequency, it is ascribed a higher uniformity index, and the vice versa. Some primers will have a high uniformity. That is, when assessing the frequency within a small window, the same (or similar) number of occurrences for a given primer will occur within different windows as in the upper sequence of FIG. 6. The upper sequence has more windows with a nearly equal frequencies, namely 4, 3, 3, 3, 4, 4 and 4 occurrences in various windows. Other primers may have uneven frequencies. These primers are said to have low uniformity. The lower sequence of FIG. 6 exemplifies this, where the number of occurrences within various windows is 3, 4, 6, 3, 7, 2, and 4. A table such as Table 3, for the different sequences of a particular length, can be generated.

TABLE 3

Frequency and Uniformity Index for 8-base fixed-sequence in a template DNA of 1 million nucleotides

| Oligonucleotide Sequence | Frequency in Template DNA | Uniformity Index |
| --- | --- | --- |
| ATGCTGAC | 1157 | .73 |
| GCTGAAGA | 1083 | .96 |
| TGATAGTA | 986 | .47 |

TABLE 3-continued

Frequency and Uniformity Index for 8-base fixed-sequence in a template DNA of 1 million nucleotides

| Oligonucleotide Sequence | Frequency in Template DNA | Uniformity Index |
| --- | --- | --- |
| ACGCGATG | 872 | .56 |
| CTTAGACT | 765 | .93 |

Sequences that have a desired frequency and a high uniformity index can be chosen from such a table, which can be expected to occur at a similar frequency and uniformity in other regions of the template.

Cycle-sequencing Long DNA Fragments by Releasing the Secondary Structure

In another embodiment, the invention is used for cycle-sequencing of a relatively long DNA, including long DNA fragments and even genomic DNA. For instance, a 10-base fixed-sequence region primer is normally expected to bind once in approximately a million bases. For example, a degenerate primer can be used for cycle-sequencing a yeast artificial chromosome (YAC) DNA, which is about one million bases in length. On the other hand, a 12-base fixed-sequence region primer, that binds 16-times more frequently than expected (i.e., 16 million bases/16=1 million bases), can be used as a fixed sequence for the same purpose. Similarly, a degenerate primer with an appropriate length fixed-sequence region can be used to sequence a sample containing genomic DNA. The length of the fixed-sequence region is determined based on the length of the genomic DNA.

Currently, however, the length of a template DNA that can be cycle sequenced is limited to about 10–20 kb. The limitation is possibly due to the secondary and/or tertiary structures of the DNA caused by the torsion in the double helix or possibly due to proteins, such as those in the nucleosomes or chromosomes, that cause further secondary and tertiary structures in long DNA molecules. The secondary and/or tertiary structures in the long DNA molecules may inhibit the primer binding and primer extension by the polymerase in such a manner that cycle-sequencing may not proceed effectively.

Releasing the secondary and tertiary structures by one of the following methods circumvents this limitation. For example, the long DNA can be cut into fragments of average sizes of 10–20 kb using restriction enzymes that cut rarely in DNA. Alternatively, partial digestion with one or more enzymes can lead to fragments that overlap. After cutting, the DNA fragments can remain in the reaction mixture, because their presence will not affect the specific binding of the primer to the target site on the particular DNA fragment in which the target site is present. Cutting a DNA such that the target sequence is present within a small enough fragment allows the cycle-sequencing of that fragment.

Alternatively, a nicking endonuclease can be used to nick the DNA. Furthermore, shearing or nebulizing of the DNA can also achieve this effect. In nicking and shearing, the DNA molecules may not be cut into smaller DNA fragments. However, these processes make it possible for the secondary and/or tertiary structures in the long DNA to be released and the primer binding and polymerase reaction to proceed in a normal fashion. In these situations, the target DNA region to be sequenced may remain intact in a fraction of the template DNA molecules, while the rest of the regions within the template molecules may be nicked or sheared at random locations. These nicks surrounding the target sequence release the secondary and tertiary structures, thereby making it available for cycle-sequencing.

PCR Amplification of Longer DNAs

In still yet another embodiment of the invention, the method is used to PCR-amplify longer DNA than is currently possible. Releasing the secondary and tertiary structures of the DNA will do this. The amount of releasing done is controlled by the frequency of the nicking, shearing, or cutting of the template DNA at random positions, such that the continuity is maintained statistically, but individual molecules are nicked at various positions mostly outside of the region to be amplified.

Participation of Degenerate Primers with Shorter than Full-length Complementarity to Template DNA in Cycle-sequencing Cycle-sequencing was done with degenerate primers in which the fixed sequence is located at the 3' end, or the 5' end, or within the primer. The results indicated that sequence data obtained with degenerate primers with the fixed sequence on the 3' end has higher signal intensity than data derived from primers having the fixed sequence on the 5' end. This data indicates the following: The full-length primers that have full complementarity may be binding with standard complementarity to the primer binding site, and may lead to the cycle-sequencing with the highest efficiency. However, it is possible that primers that have one or a few nucleotide mismatches may be able to bind to the specific target primer-binding site, and may lead to efficient cycle-sequencing. See FIG. 3B. This may be truer for primers with mismatches at the 5' end, especially at the farthest 5' end, compared to those at the 3' end. See FIG. 3B. Thus, because more primers (i.e., those with full complementarity and those with partial complementarity) can bind, higher signal intensity might result. While it has been shown that stronger sequencing data is obtained with the fixed sequence at the 3' end, the invention is not limited to having the fixed sequence on this end.

Referring to FIGS. 3A and 3B, the mismatches on the 5' end can be anywhere from one to a few nucleotides. The fraction of primers with one or a few mismatches anywhere on the 5' half of the degenerate primer is significant. In conjunction with the fixed 3' half of the primer, the 5' half of the primer with most complementarity will aid greatly in the overall correct priming of a primer species for PCR or for sequencing. In a 16-base primer with 8 fixed bases on the 3' end and 8 randomized bases on the 5' end, one nucleotide mismatch at the farthest 5' end will leave a primer of 15 bases that is fully complementary. A two-nucleotide mismatch at the farthest 5' end will leave a primer of 14 bases, and so on. Because cycle-sequencing is carried out at a slightly lower temperature of annealing (~50° C.), the primers with slightly shorter complementarity may bind with the efficiency needed for good priming and initiation of polymerization. This may happen up to a mismatch of even 8–10 nucleotides.

The number of possible primers with 8 randomized sequences is $4^8$ (~64,000 different primer sequences). The number of primers that have full-length complementarity to a given target sequence is one in 64,000. The number of primers that include one nucleotide mismatch at the farthest 5' end is 3 (4−1; the $4^{th}$ primer is the full-length complementary primer). See FIG. 3B. The number of primers with 2 nucleotide mismatches at the farthest 5' end is 15 ($4^2$−1), with 3 nucleotide mismatches is 63 ($4^3$−1). The number of primers with 6 nucleotide mismatches is 4095 ($4^6$−1), and so on. Thus, the fraction of primers with an 8-base fixed sequence in a degenerate primer of 16 bases that have at least 10 bases fully complementary to the binding site is $\frac{1}{16}$ of all possible primers (¼ of the primers with the first additional base and ¼ of the primers with the second additional base). Therefore, by using only a 16-fold higher quantity of the degenerate primer compared to the standard quantity for a full-length primer usually used, one can achieve the efficiency of the standard cycle-sequencing. In fact, good sequencing results were generated even when a slightly reduced concentration of an 8-base fixed-sequence region primer compared to that used in a regular cycle-sequencing reaction was used.

Others have attempted to use primers that are shorter than standard primers for cycle-sequencing. However, these primers are ineffective, probably because of the specificity and affinity of binding of shorter primers to template DNA may be significantly lower compared to those for longer, standard-length primers. For instance, sequences from a nanomer sequence primer library generate poor sequencing results. See, e.g., Siemieniak and Slighton, 1990. Primer walking using octomers has been attempted. See, e.g., Hardin, et al., 1996; Jones and Hardin, 1998. However, only a subset of octamer primers is effective in cycle-sequencing, again probably due to similar reasons. In the current invention, almost any degenerate primer with a 7- or 8-base fixed-sequence region degenerate primer will be able to prime cycle-sequencing, because the actual primers that participate in the priming reaction are much longer, for example, primers with a 13- to 18-base fixed-sequence regions. Even a degenerate primer with a 5- or 6-base fixed-sequence region primer can be expected to prime cycle-sequencing, because the actual length of complementarity of primers that will participate in the priming reaction may be a 10 or longer bases. There will be at least a small fraction of full-length primers that will participate in the priming reaction, which may have a significant effect in priming and cycle-sequencing. The fraction of primers available in the primer preparation with one to a few mismatches at the extreme 5' ends is significant. See FIG. 3B. A significant fraction of 13-base fixed-sequence region primers or longer are available. These primers bind with a vastly higher efficiency compared to the octamer or nanomer primers. Some mismatched nucleotides may not bind to the complementary sequence and may be hanging and free-floating. However, they will not adversely affect the priming reaction either. Thus, this method provides many species of primers with significantly longer complementarity than the fixed-base sequence itself, with a higher ability to prime a cycle-sequencing or amplification than traditional short fixed-base sequences.

Using a Handle on a Degenerate Primer with a Partly-fixed Sequence

Figure 7:
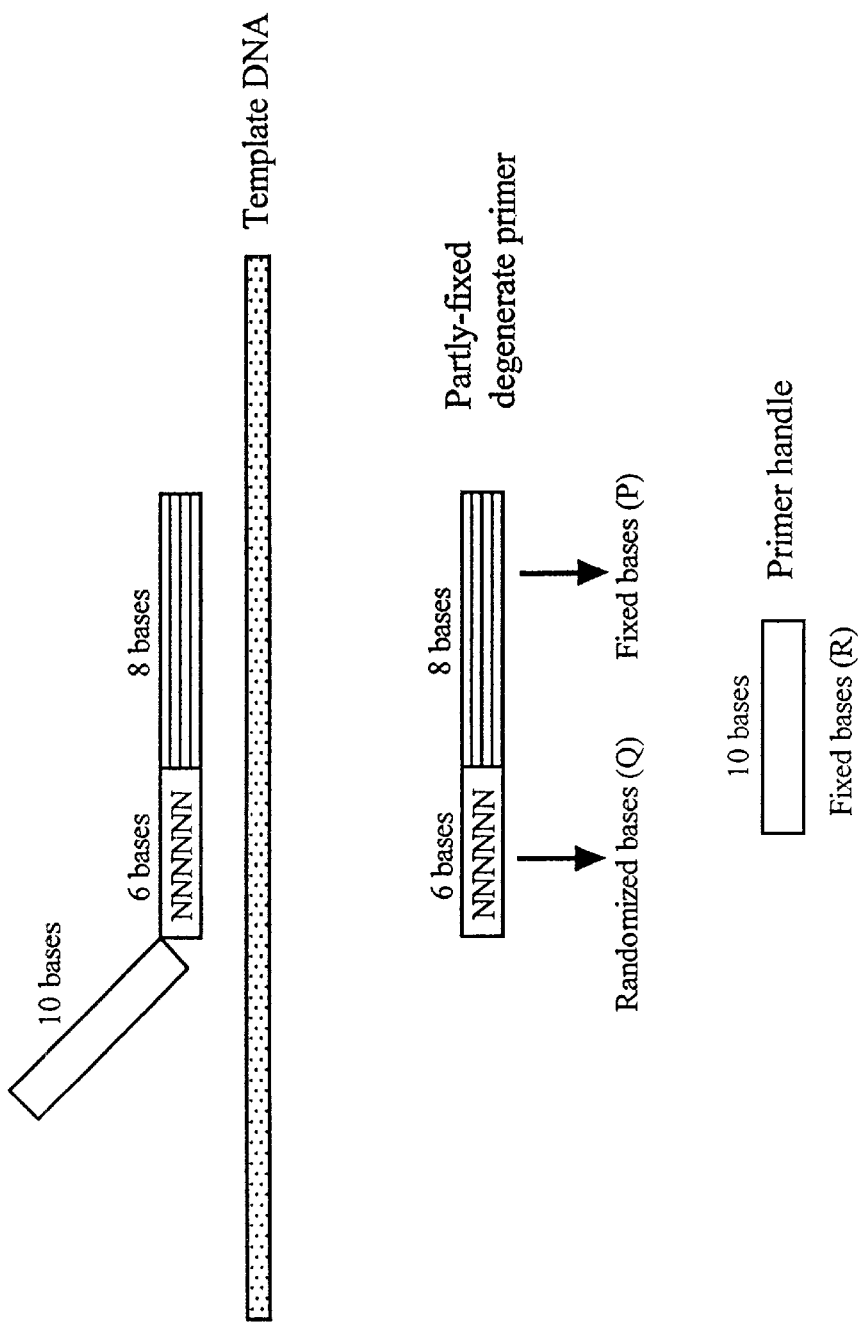
FIG. 7 is a schematic showing the use of a handle on the degenerate primer with a party-fixed sequence.

Within certain limits, longer primers are more advantageous than shorter primers in PCR. To provide even longer primers, a degenerate primer with a partly-fixed sequence can be used that also contains a handle at the 5' end. Adding a few universal bases (e.g., 5-nitroindole, inosine) to the 5' or 3' ends of primers, or within the interior sequence of a primer, aids in their binding affinity because each universal base can complement with any of the four bases at a given nucleotide location. Referring to FIG. 7, still another embodiment of this invention is a method for PCR amplifying an unknown DNA using a first primer with a partly-fixed sequence containing a handle at one end. The second primer is a partly-fixed degenerate primer with a short-fixed sequence, which may also have a handle.

In the example given, a primer having a fixed sequence of 8 bases, a randomized sequence of 6 bases, and a handle of 10 bases is used. These numbers are used to illustrate the invention, and can considerably vary. At the standard stringent temperate, a PCR between such a first primer and a second primer that has 5-fixed bases and the rest randomized, will amplify the DNA between them. In the first step of amplification, DNA will be synthesized from the first base, represented by the first N in the degenerate primer (of the first primer). In this first PCR cycle (i.e., first strand synthesis), the handle sequence does not participate in binding. However, in the second PCR cycle (i.e., second strand synthesis), the complementary strand will be synthesized until the 5' end of the handle. The last 10 bases synthesized are complementary to the handle. From the second cycle of amplification, the primer that will function at this end as a full-length primer will include the sequence of the handle, the actual sequence at the NNNNNN, and the fixed sequence. Thus, starting at the second cycle of amplification, the actual primer at work at this end will be all of the 26 bases, namely, 10 bases (handle)+6 bases (actual bases at the 6 N's, complementary in the template DNA)+8 bases (fixed bases).

The annealing temperature of the PCR can be adjusted to reflect the $T_m$ of the partial primer sequence (N's+fixed bases) for the first PCR cycle, and to reflect the $T_m$ of the complete primer (handle+N's+fixed bases) starting at the second PCR cycle. The $T_m$ for the partial fixed primer can be predicted as described above. The same holds true for the second primer with a handle. The $T_m$s of the first and second primers, each with handles, can be designed to match as closely as possible.

Optionally, instead of using all N's at the randomized positions, we can use R (purines) or Y (pyrimidines). Alternately, ionisine, 5-nitroindole, and other rare bases or synthetic nucleotides can also be used as "universal bases," which can bind with any of the four bases. These bases can also be used to statistically adjust the length of the DNA fragment in which a given primer occurs once. For example, a 4-base fixed-sequence region with additional 4 N's linked to it will occur once in 256 bases. This primer with additional 4 R's or Y's will occur once in 4096 bases. Thus, longer full-length primers can be generated for PCR or cycle-sequencing. Optionally, the second, partly-fixed degenerate primer can also have a primer handle.

Simultaneous Sequencing of a Template DNA at Multiple Sites in the Same Reaction Vessel:

The current invention will be able to adapt to many advances in cycle-sequencing or PCR. For instance, using the dye-primer chemistry, wherein primers are dye labeled, multiple sequencing reactions can be electrophoresed on the same lane of a gel. With dye-terminator chemistry, the terminators (i.e., the ddNTPs) are dye labeled, and sequencing reactions for A, T, C, or G can be electrophoresed on the same lane of a gel. With both chemistries, the sequencing fragments are identified by the respective dyes. Traditionally, the sequencing reactions from an individual template is either run in four separate lanes (if there is no way to distinguish the individual termination reactions) or in a single lane (if there is a way to distinguish them). Only one DNA sequence (of ~500 bp) can be obtained from one lane of a gel. Because dye-primer chemistry allows for the identification of different DNA fragments labeled with specific dyes, sequence data from multiple templates can be processed on the same gel lane.

In this embodiment, for each set of sequencing reactions (i e., the A, G, T, and C termination reactions) the sequencing primer has a different dye from a unique set of four dyes. Additional sets of sequencing reactions have different, unique sets of four dyes. Sequencing fragments from different degenerate primers (thus, from different templates) can be combined in one tube and electrophoresed on the same gel lane, thereby reducing the number of gel lanes necessary to run sequencing reactions from individual templates. The throughput of each gel lane is increased accordingly. Thus, a given unknown template DNA can be simultaneously sequenced at multiple locations using multiple primers with different dyes. Because the current invention can use multiple degenerate primers each with a different fixed sequence, the template DNA can be sequenced at multiple locations simultaneously in the same reaction vessel. For a 10–20 kb DNA template, 10–20 multiple reactions can be done in one tube. Even though four separate tubes would be needed in dye-primer chemistry to carry out the four termination reactions (i.e., the G reaction, the C reaction, the A reaction, and the T reaction), this still reduces time, labor, and cost of sequencing significantly.

The current invention is also applicable to DNA molecules where a short region sequence is known from which degenerate-primer walking can be continued. For example, this procedure can be used to obtain complete sequences of cDNA where expressed sequence tags (ESTs) are known, even from a CDNA library. A cDNA molecule can be sequenced from DNA pooled from a cDNA library, even with all other CDNA molecules present in the same reaction mixture Adding Universal Bases at the ends of Degenerate Primers.

Optionally, universal bases as described above can be added to the degenerate primer, which will enhance the primer's binding affinity. These universal bases can be added at the 5' end, the 3' end, at both ends of the primer, or within the primer. The binding affinity of the full-length primer species within the degenerate primer preparation of, for example, a 16–20 base primer is already fairly high. Therefore, an even higher temperature can be used for the annealing reaction ($T_a$ or $T_m$) for the tailed primers, compared to those used for standard length primers. This higher stringency of $T_a$ or $T_m$ will avoid non-specific binding of the primer. The ratio of the number of universal bases to the total length of the primer is low in the case of the degenerate primers compared to adding a tail to an octamer or nonamer primer. Thus, the specificity of the actual primer is not reduced. The ratio of the total primer length to the number of universal bases in the current invention is much higher than for the octamer or nanomer to which universal bases tails are added. Adding universal bases will allow the availability of even longer primers than provided by the full-length primers in the partly-fixed degenerate primers with full complementarity. For instance, if 3 universal nucleotides are added at the end of a 16 base primer with 8-fixed nucleotides, it will effectively increase the total length of the primer to 19.

Figures 8A, 8B:
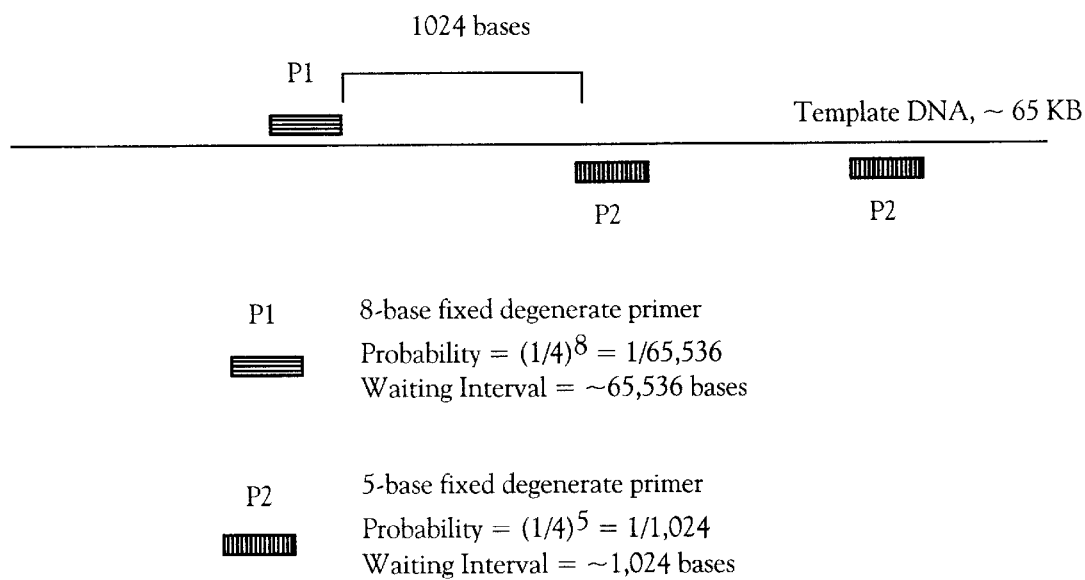
FIG. 8A is a schematic of partly-fixed primers used as the second primer along with a first primer.
FIG. 8B is a schematic illustrating the statistically predicted waiting interval of an 8-base fixed degenerate primer and a 5-base fixed degenerate primer

Amplification of DNA with a First Degenerate Primer and a Second Degenerate Primer Having a Fixed Region that is Shorter than the Fixed Region of the First Primer Referring to FIGS. 8A and 8B, in still yet another embodiment of the invention, a first set of primers having a fixed region and a randomized region as described above is used. In addition, a second set of primers also having a fixed region and a randomized region is used. However, the second set of primers has a shorter fixed region than the fixed region of the first primer set, see FIG. 8B. The first set of primers contains a primer with a fixed sequence that will bind, on average, only once to the DNA template. This is shown in FIG. 8B as a first plurality of 8-base fixed degenerate primers which will bind statistically only once in a template DNA of about 65 kb. The second plurality of primers has a 5-base fixed region, which will, speaking, bind about once per 1,000 bases. The two primer sets prime a PCR amplification reaction. Optionally, the first set of primers can be labeled with a fluorescent dye so that when a sequencing reaction is performed on the PCR products, the labeled primer set primes the sequencing reactions. The resulting series of sequencing fragments are labeled. A handle, as described above, can also be added to one or both sets of primers. Preferably, the handle is added to the 5' end of the primers. The length of the PCR product depends on the length of the fixed-base region of the second primers. In FIG. 8B, a 5-base fixed-sequence region primer is used, which has a probability of binding every $4^5$ (1024) bases. This results in a PCR product that is about 1,000 bases long. Preferably, primers that bind approximately 1,000 to 5,000 bases apart are used, and more preferably, primers that bind 10,000 to 50,000 bases apart are used.

BIBLIOGRAPHY

Ball, S., et al., 1998. The use of tailed octamer primers for cycle-sequencing, *Nucleic Acids Research* 26:5225–5227.

Burbelo, P. D. and Iadarola, M. J., 1994. Rapid plasmid DNA sequencing with multiple octamer primers, *Biotechniques* 16:645–6; 648–50.

Hardin, S. H., et al., 1996. Octamer-primer cycle-sequencing: Design of an optimized primer library, *Genome Research*, 6:545–550.

Hon, W. and Smith, L. M., 1994. DNA sequencing with a hexamer string primer and dye-labeled terminators. *Anal Biochem.* 221:136–141.

Jones, L. B. and Hardin, S. H., 1998. Octamer-primed cycle-sequencing using dye-terminator chemistry, *Nucleic Acids Research*, 26:2824–2826).

Kaczorowski, T. and W. Szybalski, 1994. Assembly of 18-nucleotide primers by ligation of three hexamers: sequencing of large genomes by primer walking. *Anal. Biochem.* 221:127–135.

Kieleczawa, J., et al., 1992. DNA Sequencing by primer walking with strings of contiguous hexamers. *Science* 258:1787–1791.

Kolter, L., et al., 1994. DNA sequencing: modular primers for automated walking. *BioTechniques* 17:554–559.

McCombie, W. R., and Kieleczawa, J., 1994. Automated DNA sequencing using 4-color fluorescent detection of reactions primed with hexamer strings, *Biotechniques* 17:574–9.

Sanger, F. & Coulson, A. R., 1975 *J. Mol. Biol.* 94:444–448.

Senapathy, P. 1986. Origin of eukaryotic introns: A hypothesis, based on codon distribution statistics in genes, and its implications, *Proc. Natl. Acad. Sci. U.S.A.* 83:2133–2137.

Senapathy, P. 1988a. Distribution and repetition of sequence elements in eukaryotic DNA: New insights by computer aided statistical analysis *Molecular Genetics (Life Sciences Advances)*, 7:53–65.

Senapathy, P. 1988b. Possible evolution of splice-junction signals in eukaryotic genes from stop codons, *Proc. Natl. Acad. Sci. U.S.A.* 85:1129–1133.

Senapathy, P., et al., 1990. Splice junctions, branch point sites, and exons: Sequence statistics, identification, and applications to the Genome Project, in *Methods in Enzymology, Computer Analysis of Protein and Nucleic Acid Sequences*, Doolittle, R. F., ed., 183:252–278.

Shapiro, M. B. and Senapathy, P., 1987. RNA splice junctions of different classes of eukaryotes: Sequence statistics and functional implications in gene-expression, *Nucleic Acids Research* 15:7155–7175.

Siemieniak, D. R. and Slightom, J. L., 1990. A library of 3342 useful nonamer primers for genome sequencing. *Gene* 96:121–124.

Studier, F. W., 1989. A strategy for high-volume sequencing of cosmid DNAs: Random and directed priming with a library of oligonucleotides. *Proc. Natl. Acad. Sci. U.S.A.* 86:6917–6921.

What is claimed is:

1. A method of sequencing a of a nucleic acid template comprising:

(a) providing a plurality of first primers, each first primer comprising (i) a region of different fixed nucleotide sequence having a defined length of from about 5 to 15 bases long and (ii) a region of randomized nucleotide sequence having a defined length of from about 2 to 11 bases long located 5' to or 3' to the region of fixed nucleotide sequence;

(b) annealing the plurality of first primers to different locations on a nucleic acid template, wherein at least one primer from within the plurality of first primers anneals specifically to the template;

(c) extending the specifically annealed primer from step (b) with a mixture of dNTPs and ddNTPs to generate a series of nucleic acid fragments; and (d) determining the nucleotide sequence of a first region of the template from the series of nucleic acid fragments.

2. The method of claim 1, wherein in step (a) is provided a plurality of first primers having a region of fixed nucleotide sequence of from about 10 to about 12 bases.

3. The method of claim 1, wherein in step (d) is determined about 500 bases of the first region of the nucleic acid template.

4. The method of claim 1, wherein in step (a) in each first primer the region of randomized nucleotide sequence contains only purine bases.

5. The method of claim 1, wherein in step (a) in each first primer the region of randomized nucleotide sequence contains only pyrmidine bases.

6. The method of claim 1, wherein in step (a) is provided a plurality of first primers wherein the region of randomized nucleotide sequence in the first primers has an unequal distribution of bases.

7. The method of claim 1, further comprising in step (b) cutting the template with a restriction enzyme prior to annealing.

8. A method of sequencing a first contig of a nucleic acid template comprising:
  (a) providing a plurality of first primers, each first primer comprising (i) a region of different fixed nucleotide sequence having a defined length of from about 5 to 15 bases long and (ii) a region of randomized nucleotide sequence having a defied length of from about 2 to 11 bases long located 5' to or 3' to the region of fixed nucleotide sequence;
  (b) annealing the plurality of first primers to different locations on a nucleic acid template, wherein at least one primer from within the plurality of first primers anneals specifically to the template;
  (c) extending the specifically annealed primer from step (b) with a mixture of dNTPs and ddNTPs to generate a series of nucleic acid fragments; and
  (d) determining the nucleotide sequence of the template from the series of nucleic acid fragments;
  (e) providing a plurality of second primers, each second primer comprising (i) a region of different fixed nucleotide sequence of from about 5 to 15 bases long and (ii) a region of randomized nucleotide sequence of from about 2 to 11 bases long located 5' to or 3' to the region of fixed nucleotide sequence;
  (f) repeating steps (b)–(d) for the second plurality of primers to thereby determine the nucleotide sequence of a second region of the template; and
  (g) assembling sequenced regions and the second, sequenced regions of the template nucleic acid to form a first contig.

9. The method of claim 8, wherein in step (f) about 500 bases of the second region of the nucleic acid template are determined.

10. The method of claim 8, further comprising:
  (h) repeating steps (e)–(g) to form a second contig;
  (i) providing a plurality of third primers, each third primer comprising (i) a region of different fixed nucleotide sequence of from about 5 to 15 bases long and (ii) a region of randomized nucleotide sequence of from about 2 to 11 bases long located 5' to or 3' to the region of fixed nucleotide sequence;
  (i) annealing the plurality of third primers to different locations on the nucleic acid template, wherein at least one primer from the third plurality annals to the template near a terminus of one of the first or second contigs;
  (k) extending the annealed third primer with a mixture of dNTPs and ddNTPs to generate a series of nucleic acid fragments; and
  (l) determining the sequence of the template between the first and second contigs from the series of nucleic acid fragments.

11. A method of sequencing a nucleic acid template comprising:
  (a) providing a plurality of first primers, each first primer comprising (i) a region of different fixed nucleotide sequence having a defined length of from about 5 to 15 bases long and (ii) a region of randomized nucleotide sequence having a defined length of from about 2 to 11 bases long located 5' to or 3' to the region of fixed nucleotide sequence;
  (b) annealing the plurality of first primers to different locations on a nucleic acid template, wherein at least one primer from within the plurality of first primers anneals specifically to the template;
    (b)(i) adding a plurality of fixed-sequence primers, each fixed-sequence primer comprising (i) a shorter region of different fixed nucleotide sequence that is shorter than the region of fixed nucleotide sequence in the first plurality of primers and (ii) a region of randomized nucleotide sequence located 5' to or 3' to the region of fixed nucleotide sequence;
    (b)(ii) annealing the plurality of fixed-sequence primers to different locations on the nucleic acid template, wherein at least one fixed-sequence primer anneals to the nucleic acid template; and
    (b)(iii) amplifying the nucleic acid template with the annealed first and annealed fixed-sequence primers with a mixture of dNTPs to amplify copies of the nucleic acid template bounded by the annealed first and fixed-sequence primers;
  (c) extending the specifically annealed primer from step (b) with a mixture of dNTPs and ddNTPs to generate a series of nucleic acid fragments; and
  (d) determining the nucleotide sequence of the template from the series of nucleic acid fragments.

12. A method of sequencing a first region of a nucleic acid template comprising:
  (a) providing a plurality of first primers, each first primer comprising (i) a region of different fixed nucleotide sequence having a defined length of from about 5 to 15 bases long and (ii) a region of randomized nucleotide sequence having a defined length of from about 2 to 11 bases long located 5' to or 3' to the region of fixed nucleotide sequence;
  (b) annealing the plurality of first primers to different locations on a nucleic acid template, wherein at least one primer from within the plurality of first primers anneals specifically to the template and wherein a sequence corresponding to or complementary to the region of fixed nucleotide sequence of the first plurality of primers occurs within the nucleic acid template at a frequency that is different than statistically predicted based on a random distribution of bases throughout the template;
  (c) extending the specifically annealed primer from step (b) with a mixture of dNTPs and ddNTPs to generate a series of nucleic acid fragments; and
  (d) determining the nucleotide sequence of a first region of the template from the series of nucleic acid fragments.

13. The method of claim 12, wherein the frequency is greater than statistically predicted based on a random distribution of the template.

14. The method of claim 12, wherein the frequency is less than statistically predicted based on a random distribution of bases throughout the template.

15. The method of claim 12, wherein binding sites complementary to the region of fixed nucleotide sequence in each primer of the plurality of first primers are distributed uniformly throughout the template.

16. A method of sequencing a nucleic acid template comprising:
   (a) providing a plurality of first primers, each first primer comprising (i) a region of different fixed nucleotide sequence having a defined length of from about 5 to 15 bases long and (ii) a region of randomized nucleotide sequence having a defined length of from about 2 to 11 bases long located 5' to or 3' to the region of fixed nucleotide sequence;
      (a)(i) relaxing torsion, secondary structure, or tertiary structure in the template;
   (b) annealing the plurality of first primers to different locations on a nucleic acid template, wherein at least one primer from within the plurality of first primers anneals specifically to the template;
   (c) extending the specifically annealed primer from step (b) with a mixture of dNTPs and ddNTPs to generate a series of nucleic acid fragments; and
   (d) determining the nucleotide sequence of a first region of the template from the series of nucleic acid fragments.

17. The method of claim 16, wherein in step (a)(i), the torsion, secondary structure, or tertiary is relaxed by shearing, nebulizing, nicking, or cutting the template.

18. The method of claim 16, wherein in step (a)(i), relaxing torsion, secondary structure, or tertiary structure in the template yields template nucleic acid fragments and the fragments remain commingled during steps (b) and (c).

19. A method of sequencing a nucleic acid template comprising:
   (a) providing a plurality of first primers, each first primer comprising (i) a region of different fixed nucleotide sequence having a defined length of from about 5 to 15 bases long and (ii) a region of randomized nucleotide sequence having a defined length of from about 2 to 11 bases long located 5' to or 3' to the region of fixed nucleotide sequence and a handle at an end of each first primer;
   (b) annealing the plurality of first primers to different locations on a nucleic acid template, wherein at least one primer from within the plurality of first primers anneals specifically to the template;
   (c) extending the specifically annealed primer from step ho) with a mixture of dNTPs and ddNTPs to generate a series of nucleic acid fragments; and
   (d) determining the nucleotide sequence of a first region of the template from the series of nucleic acid fragments.

20. The method of claim 19, wherein the handle is at the 5' end of each first primer.

21. The method of claim 20, wherein the handle is one or more universal bases.

22. The method of claim 21, wherein the universal base is selected from the group consisting of inosine and 5-nitroindole.

23. The method of claim 20, wherein the handle is one or more purine bases.

24. The method of claim 20, wherein the handle is one or more pyrimidine bases.

25. A method for amplifying a nucleic acid template comprising:
   (a) providing a plurality of fast primers, each first primer comprising (i) a region of different fixed nucleotide sequence having a defined length of from about 5 to 15 bases long and (ii) a region of randomized nucleotide sequence having a defined length of from about 2 to 11 bases long located 5' to or 3' to the region of fixed nucleotide sequence;
   (b) providing a plurality of second primers, each second primer comprising (i) a region of different fixed nucleotide sequence having a defined length of from about 5 to 15 bases long and (ii) a region of randomized nucleotide sequence having a defined length of from about 2 to 11 bases long located 5' to or 3 ' to the region of fixed nucleotide sequence, wherein the regions of fixed nucleotide sequence in the second plurality of primers is shorter than the regions of fixed nucleotide sequence in the first plurality of primers; and
   (c) amplifying a first region of the nucleic acid template with the plurality of first primers and the plurality of second primers, wherein at least one primer from within each of the plurality of first primers and the plurality of second primers anneals specifically to the template.

26. The method of claim 25, wherein in step (a) is provided a plurality of first primers that is labeled and further sequencing the nucleic acid template with at least one annealed, labeled first primer.

27. The method of claim 25, further wherein in step (a) is provided a plurality of first primers having a handle at an end of the plurality of first primers.

28. The method of claim 27, wherein the handle is located at the 5' end of the plurality of first primers.

29. The method of claim 25, wherein in step (b) the distance between annealing sites of a first plurality of primers and a second plurality of primers is at least 1000 bp.

* * * * *